US009453837B2

(12) United States Patent
Belle et al.

(10) Patent No.: US 9,453,837 B2
(45) Date of Patent: Sep. 27, 2016

(54) GRAFTED DINUCLEAR METAL COMPLEXES, AND USE THEREOF AS CELLULAR MICROPARTICLE SENSORS

(75) Inventors: Catherine Belle, Beaulieu (FR); Gisele Gellon, Saint-Martin d'Heres (FR); Laurent Plawinski, Epinay sur Odon (FR); Loic Doeuvre, Luc sur Mer (FR); Eduardo Angles Cano, Paris (FR)

(73) Assignees: CENTRE NATIONAL DE LA RECHERCHE SCIENTIFIQUE (CNRS), Paris (FR); UNIVERSITE DE CAEN BASSE-NORMANDIE, Caen (FR); UNIVERSITE JOSEPH FOURIER, Grenoble (FR)

( * ) Notice: Subject to any disclaimer, the term of this patent is extended or adjusted under 35 U.S.C. 154(b) by 239 days.

(21) Appl. No.: 14/006,387

(22) PCT Filed: Mar. 23, 2012

(86) PCT No.: PCT/FR2012/050610
§ 371 (c)(1),
(2), (4) Date: Sep. 20, 2013

(87) PCT Pub. No.: WO2012/127175
PCT Pub. Date: Sep. 27, 2012

(65) Prior Publication Data
US 2014/0011219 A1    Jan. 9, 2014

(30) Foreign Application Priority Data
Mar. 23, 2011 (FR) ...................... 11 00873

(51) Int. Cl.
*G01N 33/543* (2006.01)
*C07D 213/38* (2006.01)
*C07D 401/14* (2006.01)

(52) U.S. Cl.
CPC ....... *G01N 33/54353* (2013.01); *C07D 213/38* (2013.01); *C07D 401/14* (2013.01)

(58) Field of Classification Search
CPC .............. C07D 213/38; C07D 401/14; G01N 33/54353
See application file for complete search history.

(56) References Cited

PUBLICATIONS

Inomata, Tomohiko et al.: "Self-assembled, monolayer electrode of a diiron complex with a phenoxo-based dinucleating ligand: observation of molecular oxygen adsorption/desorption in aqueous media", Chemical Communications (Cambridge, United Kingdom) , (3). 392-394 Coden: CHCOFS; ISSN: 1359-7345, 2008, XP002640577, p. 392; compounds 1,2, Cited in ISR.
Kwon, Tae-Hyuk et al.: "Phosphorescent thymidine triphosphate sensor based on a donor-acceptor ensemble system using intermolecular energy transfer", Chemistry—A European Journal, 14 (31). 9613-9619 Coden: CEUJED; ISSN: 0947-6539, 2008, XP002640578, p. 9615; compounds 2,3, Cited in ISR.
International Search Report, dated May 24, 2012, from corresponding PCT application.

*Primary Examiner* — Shafiqul Haq
(74) *Attorney, Agent, or Firm* — Young & Thompson

(57) ABSTRACT

Novel grafted dinuclear metal complexes having formula (I) or of formula (II)

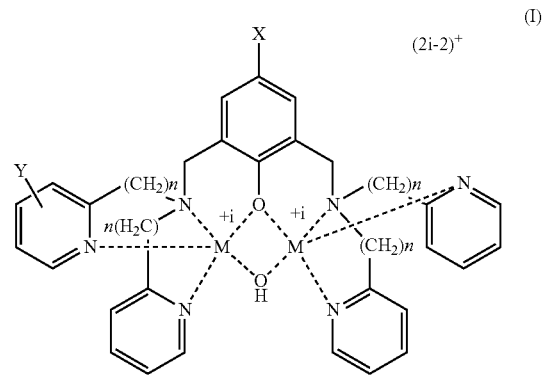

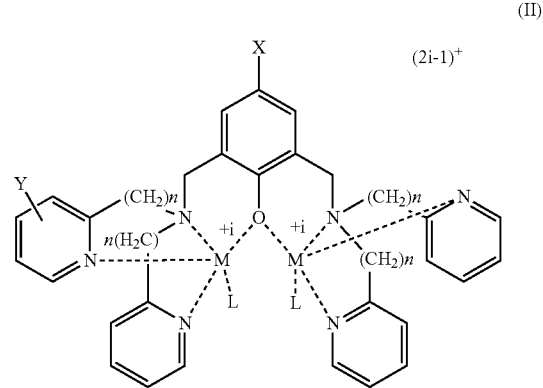

wherein M represents a metal ion,
and also the use thereof as sensors in a method for detecting and/or characterising cellular microparticles.

6 Claims, 2 Drawing Sheets

GRAFTED DINUCLEAR METAL COMPLEXES, AND USE THEREOF AS CELLULAR MICROPARTICLE SENSORS

FIELD OF THE INVENTION

The invention relates to novel grafted dinuclear metal complexes and use thereof as sensors in a method for the detection and/or characterisation of cellular microparticles in support (or heterogeneous) medium or in solution.

The terms "cellular microparticle" or "cellular microvesicle" may be used interchangeably. For the sake of convenience, the term "microparticle" or "cellular microparticle" shall be used in the following description.

BACKGROUND OF THE INVENTION

Cellular microparticles are membrane microvesicles released in biological fluids during cell activation or during apoptosis, in the course of various pathological conditions, including inflammation or diseases associated with impaired vascular function.

These microparticles are released into the extracellular space after a remodelling of the cell membrane, thus exposing on the outer leaflet phosphatidylserine, which is normally present on the inner leaflet, as well as other identity markers of their cellular origin.

Cellular microparticles are submicron sized (0.1-1 μm). Although they are present in the biological body fluids, especially in the circulating blood of healthy individuals, their presence in high levels is associated with various thrombotic, inflammatory and metabolic disorders and with cancer. Besides cancer, these diseases are numerous and range from diabetes and its vascular complications to inflammatory diseases, including atherosclerosis. It concerns, in particular, cardiovascular disease with increased risk of thrombosis or even neurovascular ischemic conditions.

Cellular microparticles may thus be considered as early markers that allow for diagnosing and assessing the risk of developing various diseases, in particular thrombotic, inflammatory and/or metabolic disorders, and thereby enable the therapeutic follow up and monitoring thereof.

Neurovascular injuries and occlusive cardiovascular diseases constitute, right after cancer, the leading causes of morbidity and mortality. In Europe and the United States, these pathologies result in significant costs in the social and economic contexts as well as in terms of public health.

These occlusive accidents are the result of a thrombus formed in situ or embolism. The formation of an occlusive thrombus was associated with localised fibrinolysis defects. However, despite the pathophysiological context, there are no reliable methodologies currently available to assess the fibrinolytic activity in the intravascular space that would enable risk assessment and prevention.

Several studies have shown that high concentrations of cellular microparticles possess good prognostic value.

Methods of detection have been established. Among the few available techniques include flow cytometry, which is the most widely used. This method partially allows phenotyping and partial quantification of cellular microparticles by means of using calibration beads. This method takes advantage of the affinity of Phophatidylserine with annexin A5, a cellular protein. More generally, antibodies directed against antigenic determinants exposed on their membranes are used.

Cellular microparticles can in particular be detected by measuring the fluorescence emitted by annexin A5 or with antibodies labelled with a fluorescent compound.

However, the sensitivity of this method does not allow for the identification of cellular microparticles having a size less than 500 nm.

Annexin A5 is also used in a "capture/quantification" test wherein the cellular microparticles which expose phosphatidylserine are captured by means of annexin A5 immobilised on the surface of microtiter plate wells (test developed by the company Hyphen Biomed).

However, this technique does not allow for the phenotype and distribution of elements to be obtained. Furthermore, its implementation is cumbersome and depends on a number of experimental factors. The capture of cellular microparticles by annexin A5 is highly dependent on calcium ions and is very sensitive to experimental variations (proteolysis, interactions with various ligands, etc.).

Thus, the detection techniques available are lacking in accuracy and sensitivity. Moreover, they are often very expensive.

It is therefore desirable to be able to detect, quantify and characterise, in particular phenotype, in an accurate and standardised manner, cellular microparticles in biological fluids.

The term "biological fluid" is understood to mean any extractable body fluid, including for example, blood, blood plasma, cerebrospinal fluid, bronchoalveolar fluid, urine, synovial fluid, breast milk, saliva, tears, seminal fluid, ascitic fluids, amniotic fluid and effusions (pleural or other). The inventors have now developed a method for detection and/or characterisation in which cellular microparticles are captured by a synthetic ligand.

SUMMARY OF THE INVENTION

The method according to the invention enables the detection and/or characterisation of cellular microparticles whatever their size. In addition, the use of a synthetic ligand makes it possible to avoid the disadvantages associated with the use of a biological molecule, such as, for example, interference with other ligands—in particular antibodies, proteolysis and even calcium sensitivity.

According to a first aspect, the invention therefore relates to grafted dinuclear metal complexes capable of recognising and binding specifically to externalised phosphatidylserine at the surface of the microparticles.

In the following sections of the description, the terms "grafted dinuclear metal complexes" or "sensors" shall be used interchangeably to define the compounds having the formula (I) or (II) here below.

The object of the invention thus relates to a compound having the following formula (I) or formula (II):

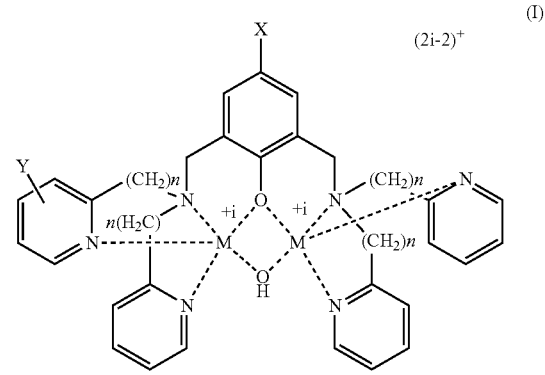

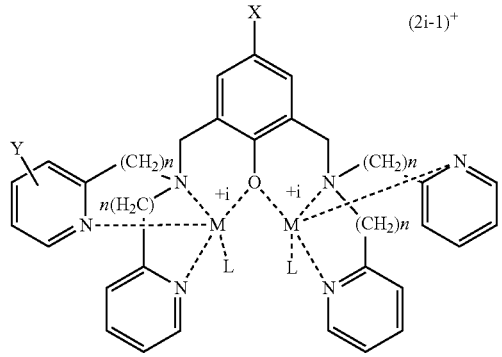

(II)

wherein $M^{+i}$ is a metal ion, and i is 1, 2 or 3

L is an exchangeable ligand

X is a —$(CH_2)_m$—NH-A group, or a —$CH_2$—NHC(O)—R—NH-A group wherein R is a $C_2$-$C_{10}$ alkyl group, preferably a $C_6$-$C_{10}$ alkyl group, either substituted or unsubstituted, linear or branched, and A is H or a fluorophore group m=1 to 12 n=1, 2 or 3 i is the charge of the metal and is 1, 2 or 3

Y is $(CH_2)_p$—$NH_2$ wherein p=0 to 12.

Preferably, M is selected from Zn, Cu, Mn, Co, Ni and Fe, Zn or Cu being preferred.

In aqueous solution, the compounds having formula (I) and (II) may be in equilibrium, depending on the pH of the medium. For example, for X=$CH_3$, n=1 and M=Cu or Zn, it may be observed that at the physiological pH, both the species are present.

They are cationic compounds whose counter ion can be selected, for example, from among the tosylate, nitrate, sulfate, sulfonate, thiosulfate, halide, hexafluorophosphate, tetraphenylborate, tetrafluoroborate anions etc.

The term "exchangeable ligand" is understood to mean a molecule that interacts weakly with the metal ions and which is available for exchange with the surrounding solution, such as a solvent molecule for example, in particular a molecule of $H_2O$ or another solvent such as, for example acetonitrile, or also a molecule dissolved in the solvent.

Indeed, the molecules present in the solution may have an affinity for a given metal ion, which results in competitive effects on the exchangeable ligands.

In the following sections of the description, the term "ligand" shall refer to the dinuclear part of the compound having formula (I) or (II) before complexation with the metal ion, and the terms "dinuclear metal complex" or "sensor" shall refer to the complexed ligand.

The compounds having formula (I) or (II) may be prepared by adapting the methods described in C. Belle et al., Tetrahedron Letters, 1994, 35, 7019-7022, for the ligand part, and in K. Selmeczi et al., Chem. Eur. J., 2007, 13, 9093-9106, with regard to the complexation. The isolation of the final complex is adapted based on the form of the compound obtained, by conventional techniques (possible precipitation, recovery of a powder, of an oil, etc.)

The method for preparation of the compounds having formula (I) or (II) may in particular comprise the following steps of:

a) synthesis of a ligand precursor of which the amino function, when A=H, is protected by a protecting group from the bis(2-pyridylmethyl)amine or BPA and 2-[3,5-Bis(chloromethyl)-4-hydroxybenzyl]isoindole-1,3-di-one, b) deprotection of the ligand thus obtained, then c) complexation of the latter with the metal ion.

As protecting group of the amine function, use will be made, for example, of a phthalimide group, tert-butyloxycarbonyl (BOC), 9-Fluorenylmethyloxycarbonyl (FMOC), acetyl, tosyl or carbamate.

BPA is commercially available and 2-[3,5-Bis(chloromethyl)-4-hydroxybenzyl]isoindole-1,3-di-one is described in the publication M. Johansson et al., Inorg. Chem. 2003, 42, 7502-7511.

The synthesis of a precursor ligand, the amine function of which is protected by a phthalimide group from BPA and 2-[3,5-Bis(chloromethyl)-4-hydroxybenzyl]isoindole-1,3-di-one may be carried out, for example, as described in Examples 1 and 2.

The X group and/or the Y group, if they/it exist(s), also known as "arm", may be grafted on the phenol unit of the ligand before complexation of the metal ion, that is, in Diagram 1, starting from compound 4.

According to one aspect of the invention, the arm grafted on the phenol unit of the dinuclear metal complex comprises a fluorophore group, such as, for example, phycoerythrin (PE) or fluorescein, especially fluorescein isothiocyanate (FITC).

The preferred compounds having formula (I) or (II) are those wherein:

M is Zn or Cu

X is —$(CH_2)_m$—NH-A, where m=1, A is H, n=1 and p=0;

X is —$(CH_2)_m$—NH-A, where m=1, A is H, n=2 and p=0;

X is —$CH_2$—NHC(O)—R—NH-A, A is H, n=1 and p=0.

When p=0, the pyridine group is not substituted by Y.

According to another aspect, the invention also relates to ligands that may be used as intermediates in the synthesis of dinuclear metal complexes having formula (I) or (II).

The object of the invention therefore also relates to compounds having formula (III) here below

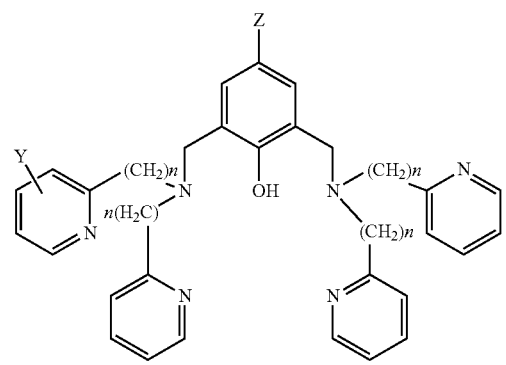

(III)

wherein

Z is $NH_2$ or a —$(CH_2)_m$—NH-A group, or a —$CH_2$—NHC(O)—R—NH-A group wherein R is a $C_2$-$C_{10}$ alkyl group, preferably a $C_6$-$C_{10}$ alkyl group, either substituted or unsubstituted, linear or branched, and A is H or a fluorophore group, provided that when m=2, A is different from H m=1 to 12 n=1, 2 or 3

Y is $(CH_2)_p$—$NH_2$ wherein p=0 to 12.

According to one aspect of the invention, the arm grafted on the phenol unit of the dinuclear metal complex comprises a fluorophore group, such as, for example, phycoerythrin (PE) or fluorescein, in particular fluorescein isothiocyanate (FITC).

The preferred compounds having formula (III) are those in which:

Z is —(CH$_2$)$_m$—NH-A, where m=1, A is H, n=1 and p=0; or

Z is —(CH$_2$)$_m$—NH-A, where m=1, A is H, n=2 and p=0; or

Z is —CH$_2$—NHC(O)—R—NH-A, A is H, n=1 and p=0.

These compounds may be prepared according to steps a) and b) of the method indicated here above.

According to a further aspect, the invention relates to a method for detection and/or characterisation of cellular microparticles, which comprises the placing in contact of a compound having formula (I) or (II)

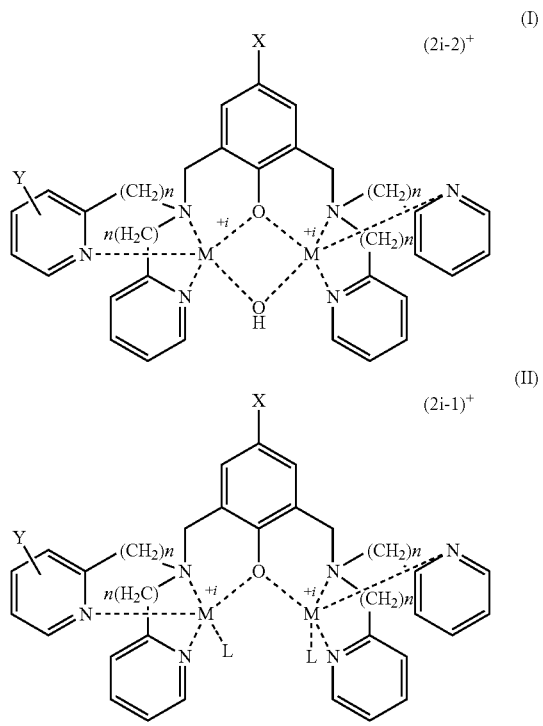

as defined here above, with a sample of biological fluid that is likely to contain cellular microparticles, and the detection and/or characterisation of the microparticles captured by the said compound having formula (I) or (II).

If necessary, the organic and inorganic phosphates, possibly present in the biological fluid, in particular blood plasma, can be chelated with chelating agents, such as for example magnesium salts, or lanthanum.

The term "detection of cellular microparticles" is understood to mean the qualitative and/or quantitative determination of the presence of said cellular microparticles in the biological fluid.

The term "characterisation of cellular microparticles" is understood to mean the identification, especially the typing, in particular the phenotyping of the said cellular microparticles, as well as, in particular, the detection of biomolecules that may be present on the microparticles, the detection of enzyme activity and the determination of RNAs.

According to a preferred aspect, the compound having formula (I) or (II) is, in a first step, immobilised on a solid support.

By way of non limiting examples, such a support may be selected from the group consisting of microtiter plates, sheets, cones, tubes, wells, beads, particles and also strips.

The invention thus relates to a method for detection and/or characterisation of cellular microparticles, which comprises the following steps:

immobilisation of a compound having formula (I) or (II) as defined here above on the surface of the solid support, placing in contact with a sample of biological fluid that is likely to contain cellular microparticles capture of the cellular microparticles on the said compound having formula (I) or (II), and detection and/or characterisation of the captured cellular microparticles.

According to a preferred embodiment, use is made of a solid support whose surface has been previously activated, such as, for example, a microtiter plate.

According to this variant, the said method of detection and/or characterisation of cellular microparticles comprises the following steps:

activation of a solid support, immobilisation of a compound having formula (I) or (II) as defined here above on the surface of the activated support, placing in contact with a sample of biological fluid that is likely to contain cellular microparticles capture of the cellular microparticles on the said compound having formula (I) or (II), and detection and/or characterisation of the captured cellular microparticles.

The activation of the support may be carried out by conventional methods, such as, for example, by using polyglutaraldehyde. Its polymeric structure enables stable polyglutaraldehyde adsorption on the support. Glutaraldehyde has reactive sites that react with the amino groups (ie, —NH$_2$) by forming covalent bonds. The activation step includes the formation of covalent bonds between at least one of the reactive sites of the polyglutaraldehyde immobilised on the solid support and the —NH$_2$ functions of the ligand. N-hydroxysuccinimide, for example, may be used as activator.

During the immobilisation step, the compound having formula (I) or (II) binds to the activated support by forming covalent bonds.

The amino group (ie NH$_2$) which is located at the end of the X arm enables the formation of imine bonds by reacting with the aldehyde groups on the surface of the activated support.

Capture of the cellular microparticles can be achieved by incubating a biological fluid that is likely to contain cellular microparticles with the compounds having formula (I) or (II), for example, by placing in suspension in a HEPES (4-(2-hydroxyethyl)piperazine-1-ethanesulfonic acid) buffer and then incubation with the sensors at ambient temperature.

The captured microparticles may then be revealed by using for example detection techniques that implement specific labelled antibodies (photometric or fluorometric analysis), an enzyme label (chromogenic analysis) or amplification techniques such as quantitative PCR or Q-PCR.

For example, the following may be used:

a) specific labelled antibodies, that is either antibodies directed against specific antigens of the original cell from which the cellular microparticles are released, called CD (for "Cluster of Differentiation"), for example CD14 antibodies for monocytes or CD105 (endoglin) for endothelial cells;

or antibodies directed against active biomolecules, for example antibodies directed against the tissue factor (TF, coagulation activator) or antibodies directed against tissue type plasminogen activators (tPA) or urokinase type plasminogen activators (uPA). These molecules are not exclusive to a given cell type, but it is important to know from the pathophysiological perspective whether they are present on the microparticle;

The antibodies may be labelled with an enzyme, such as, for example, peroxidase, and then detected by spectrophotometric analysis using a suitable substrate. These antibodies may also be labelled with a fluorochrome and detected by fluorescence;

b) a chromogenic test: this test enables the detection of the activity of an enzyme with the use of a synthetic substrate.

For example, plasminogen activators tPA or uPA convert plasminogen into plasmin (thrombolytic and fibrinolytic enzyme) and this plasmin can be detected by using a chromogenic substrate. Thus, by adding to the captured microparticles, plasminogen and a synthetic chromogenic substrate sensitive to plasmin, the activity of tPA and uPA may be detected. This technique enables the detection of molecules with enzymatic activity found on the surface of the microparticles.

c) the Q-PCR technique: the mRNAs and microRNAs present within the captured microparticles can be detected by means of specific primers. The RNAs are released by bursting microparticles by means of a temperature gradient during the first cycling of temperature of the Q-PCR, and then amplified specifically using primers with which they are placed in contact on the support and the action of the polymerase.

According to a variant of the detection method mentioned here above, immobilisation is carried out on the solid support as defined here above of a compound having formula (III) as defined here above, that is to say, a ligand, and the support-ligand ensemble is incubated in the presence of the metal ion, in a manner such that the dinuclear metal complex having formula (I) or (II) is formed in situ.

In this variant, it is possible, for example, to immobilise the ligand having formula (III) on the solid support by incubation for a period of about 2 hours at ambiant temperature, of about 20° C. to 25° C., then remove the excess ligand, and incubate the metal ion with the support-ligand ensemble for about 2 hours at the same temperature.

Then the detection method subsequently comprises the steps mentioned here above, namely the placing in contact of said compound having formula (I) or (II) with a sample of biological fluid that is likely to contain cellular microparticles, the capture of the cellular microparticles on the said compound having formula (I) or (II), and the detection and/or characterisation of the captured cellular microparticles.

According to another aspect of the invention, the compound having formula (I) or (II) is used in a solution.

Use would then be made, preferably, of a compound having formula (I) or (II) wherein X is —(CH$_2$)$_m$—NH-A, —CH$_2$—NHC(O)—R—NH-A wherein R is a C$_2$-C$_{10}$ alkyl group, preferably a C$_6$-C$_{10}$ alkyl group, either substituted or unsubstituted, linear or branched, and A is a fluorophore group.

The captured microparticles may, for example, be detected by measuring fluorescence with the use of specific antibodies, possibly labelled with fluorophores.

According to a further aspect, the invention also relates to a method for detection and/or characterisation of cellular microparticles that enable the assessment of the risk of developing various diseases and/or the therapeutic follow up and monitoring thereof, in particular thrombotic, inflammatory and/or metabolic disorders, or even cardiovascular or neurovascular diseases and events, or diseases such as diabetes, cancer, Alzheimer's disease or other pathologies.

Advantageously, the method for detection and/or characterisation of cellular microparticles that enables the assessment of the risk of developing various diseases and/or the therapeutic follow up and monitoring thereof comprises the following steps:

the placing in contact of a compound having formula (I) or (II)

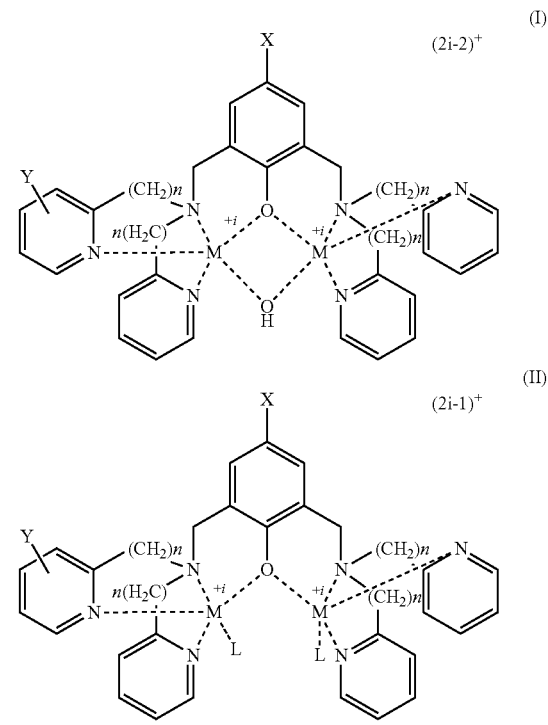

as defined here above with a sample of biological fluid that is likely to contain cellular microparticles, the detection and/or characterisation of the captured microparticles by the said compound having formula (I) or (II), and the comparison of results of the measurement performed in the previous step with the results of a similar measurement performed on a control sample of biological fluid.

The invention also relates to a method for diagnosis, and assessment of the risk of developing various diseases and/or the therapeutic follow up and monitoring thereof, in particular thrombotic, inflammatory and/or metabolic disorders, or even cardiovascular or neurovascular diseases and events, or diseases such as diabetes, cancer, Alzheimer's disease or other pathologies, comprising the following steps:

the placing in contact of a compound having formula (I) or (II) as defined here above with a sample of biological fluid that is likely to contain cellular microparticles, the detection and/or characterisation of the captured microparticles by the said compound having formula (I) or (II), and the comparison of results of the measurement performed in the previous step with the results of a similar measurement performed on a control sample of biological fluid.

The conditions for the placing in contact of a compound having formula (I) or (II) with cellular microparticles, as well as for capture, detection and/or characterisation of the said cellular microparticles are as defined here above.

Advantageously, the control biological fluid is a biological fluid that is identical to that tested, but derived from an individual considered to be healthy. Alternatively, the control biological fluid is from the same individual as the biological fluid tested, but is derived from an earlier sample.

Potential uses of the method for detection and/or characterisation of cellular microparticles according to the invention are, for example, early diagnosis and therapeutic follow up and monitoring of a risk of thrombosis, which may cause a myocardial infarction or stroke, or diseases such as diabetes, cancer, Alzheimer's disease or other diseases.

DETAILED DESCRIPTION OF THE INVENTION

Figure 1:
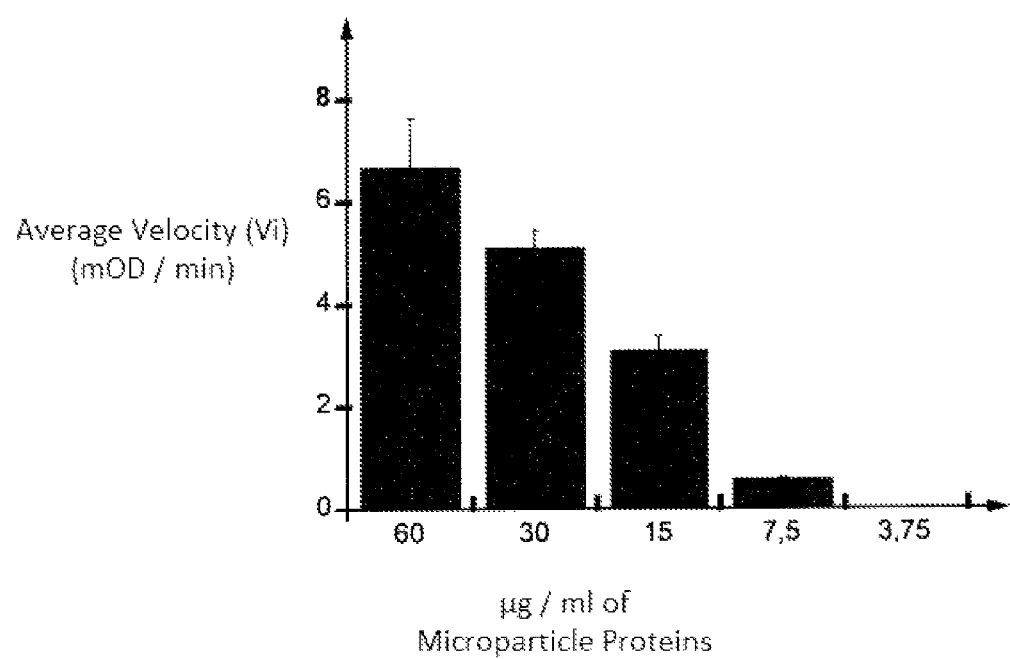
FIG. 1 shows the detection of a dilution of microparticles that is based on the amount of proteins, by photometric analysis. The essay consists of a colorimetric assay of cellular microparticles by immobilisation of a Zn complex of the invention on a microtiter plate (sensitivity study).

The invention is illustrated by but in no way limited to the following examples.

EXAMPLE 1

Preparation of the Ligand Having Formula (III)

4-(aminomethyl)-2,6-bis[[bis(2-pyridyl methyl)amino]methyl]phenol HBPMP-NH$_2$

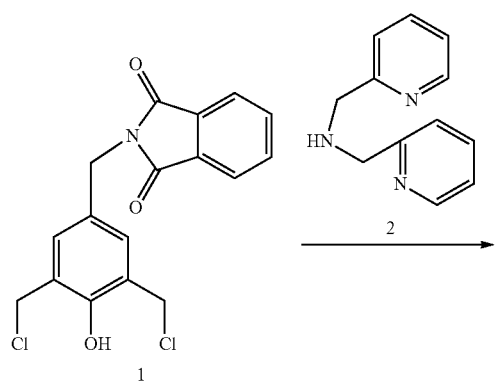

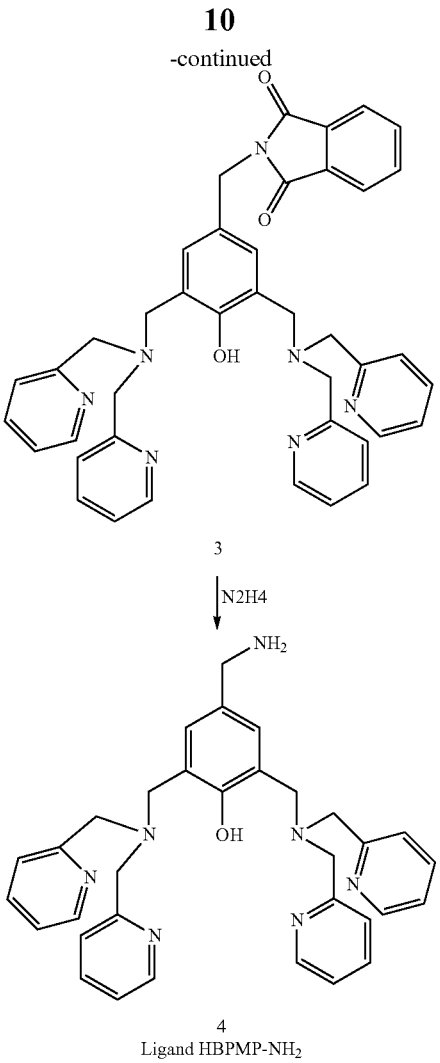

4
Ligand HBPMP-NH$_2$ 1) 2-{4-hydroxy-3,5-bis[[bis(2-pyridylmethyl) amino]methyl]benzyl}isoindole-1,3-dione, (3)

The compound 1 is described in the publication M. Johansson et al., Inorg. Chem., 2003, 42, 7502-7511.

In a 500 mL three neck flask in an inert argon atmosphere and immersed in an ice bath, 6.5 g (1 equiv.) of dichloro precursor (1) is introduced in 120 mL of dry Tetrahydrofuran (THF). In the addition funnel 60 mL of dry THF is placed within which 6.9 g (2 equiv.) BPA (compound 2) as well as 10 mL of triethylamine (4 equiv.) were dissolved. The addition is carried out drop by drop at 0° C.

At the end of the addition, the brown suspension obtained is left to be stirred at ambient temperature for 24 hours. After filtration and rinsed with THF, the filtrate is recovered, which is evaporated.

The resulting solid is purified on a neutral alumina column (height: 11 cm, diameter 4.5 cm) deactivated by a mixture of 1% H$_2$O, 10 mL of MeOH, 150 mL of EtOAc and 200 mL of cyclohexane. The elution solvents are: EtOAc+ cyclohexane 1/2, v/v, EtOAc+cyclohexane 1/1, v/v, EtOAc and EtOAc with 1 to 2% MeOH.

After evaporation, 7.85 g (66%) of pure product 3 is recovered in the form of a white solid.

$^1$H NMR (300 MHz, CD$_3$CN, δ ppm): 11.15 (s, 1H, OH); 8.43 (d, 4H, Py-N—CH); 7.83 (m, 4H, Pht); 7.59 (td, 4H, Py); 7.41 (d, 4H, Py-C—CH); 7.20 (s, 2H, Ar—H); 7.15 (m, 4H, Py-N—CH—CH); 4.46 (s, 2H, Pht-CH$_2$); 3.84 (s, 8H, Py-CH$_2$); 3.77 (s, 4H, Ar—CH$_2$—N).

$^{13}$C RMN (75 MHz, CD$_3$CN, δ ppm): 168.3 (C=O); 159.4 (Py-C); 155.9 (C—OH); 149.0 (Py-N—CH); 136.8 (Py); 134.1 (Py); 132.5 (CO—C); 129.8 (Py-C—CH); 126.6 (Ar—C—CH$_2$); 124.6 (Ar—C—CH$_2$); 123.5 (Pht-CH); 123.3 (Pht-CH); 122.2 (Ar—CH); 60.1 (Ar—CH$_2$-Pht); 54.8 (Py-CH$_2$); 41.6 (Ar—CH$_2$—N).

ESI (Electrospray ionisation) mass spectrum, m/z=676 (M+H)$^+$.

2) 4-(aminomethyl)-2,6-bis[[bis(2-pyridylmethyl)amino]methyl]phenol (4)

In a 500 mL flask fitted with a condenser, 6.5 g of the protected product (3) (1 equiv.) and 250 mL of absolute ethanol are introduced. 20.5 mL of hydrazine monohydrate (4 equiv.) in 10 mL of absolute ethanol is added drop by drop, then the reaction medium is heated under reflux and left to be stirred for two hours and then overnight at ambient temperature.

The white suspension obtained is filtered, rinsed with ethanol and the filtrate is evaporated. The residue is taken up in 150 mL of a solution of 2 N sodium hydroxide and left to be stirred for two hours. The reaction medium is neutralised with a solution of 4N HCl to pH 7. The solution is extracted three times with dichloromethane, and then dried over Na$_2$SO$_4$ and evaporated.

5 g (95%) of compound 4 is obtained in the form of a white solid.

$^1$H NMR (300 MHz, CDCl$_3$, δ ppm): 8.55 (d, 4H, Py-N—CH); 7.57 (t, 4H, Py); 7.45 (d, 4H, Py-N—C—CH); 7.16 (s, 2H, Ar—H); 7.10 (t, 4H, Py); 5.29 (s, 1H, OH); 3.98 (s, 2H, NH$_2$—CH$_2$); 3.84 (d, 8H, Py-CH$_2$); 3.77 (s, 4H, Ar—CH$_2$—N); 2.89 (s, 2H, NH$_2$).

$^{13}$C NMR (75 MHz, CDCl$_3$, δ ppm): 159.6 (Py-C); 155.3 (C—OH); 148.8 (Py-N—CH); 136.6 (Py-N—C—CH—CH); 130.0 (Ar—C—CH$_2$—NH$_2$); 129.0 (Ar—NH$_2$); 124.1 (Ar—C—CH$_2$—N); 123.1 (Pyr-C—CH); 122.0 (Py-N—CH—CH); 59.8 (Py-CH$_2$); 54.7 (Ar—CH$_2$—N); 45.1 (NH$_2$—CH$_2$). ESI mass spectrum, m/z=568 (M+Na)$^+$, 546 (M+H)$^+$.

EXAMPLE 2

Preparation of the complex [μ-[4-(aminomethyl)-2,6-bis[[bis(2-pyridylmethyl)amino]methyl]-phenolato]]-μ-hydroxo, dizinc, diperchlorate. (5) [(Zn$_2$)(BPMP-NH$_2$)(μ-OH)].(ClO$_4$)$_2$

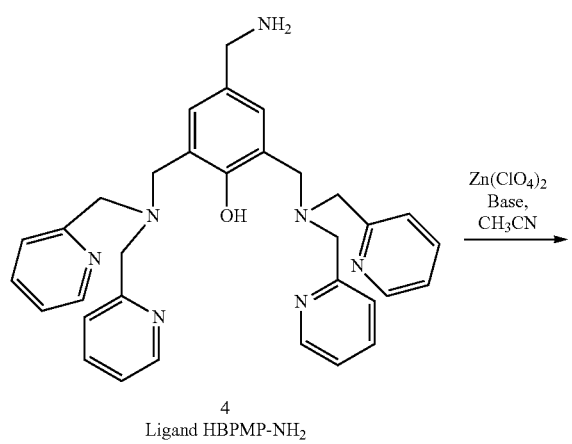

4
Ligand HBPMP-NH$_2$

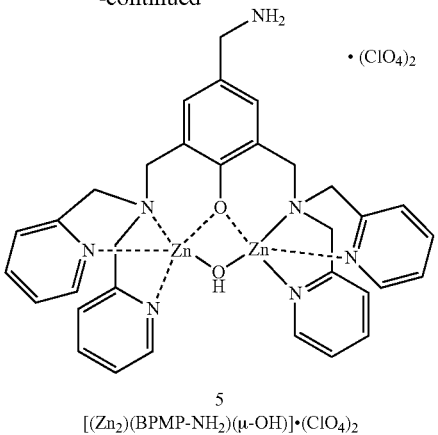

5
[(Zn$_2$)(BPMP-NH$_2$)(μ-OH)]•(ClO$_4$)$_2$

In a 25 mL flask the ligand 4 (0.4 g, 1 equiv.) dissolved in 8 mL of acetonitrile and 0.155 g (2.1 equiv.) of triethylamine is introduced.

0.57 g (2.1 equiv.) of zinc perchlorate hexahydrate dissolved in 6 mL of acetonitrile is added therein drop by drop. Upon completing the addition of perchlorate, the mixture is left to be stirred at ambient temperature. The solution is partially evaporated so as to have a volume of about 5 ml and then ethyl ether is added therein until a certain cloudiness is observed after which it is left at −20° C. overnight.

A precipitate is obtained which is filtered, rinsed with ethyl ether and dried. The filtrate is subjected again to the same treatment, which eventually allows for the recovery of 280 mg (43%) of compound 5 in the form of a pale yellow powder.

$^1$H NMR (300 MHz, CD$_3$CN, δ ppm): 8.98 (d, 4H, Py-H); 8.05 (t, 4H, Py-H); 7.65 (t, 4H, Py-H); 7.53 (d, 4H, Py-H); 7.09 (s, 2H, Ar—H); 4.01 (s, 8H, Py-CH$_2$); 3.91 (d, 2H, NH$_2$—CH$_2$); 3.84 (s, 4H, Ar—CH$_2$—N).

$^{13}$C NMR (75 MHz, CD$_3$CN, δ ppm): 163.4 (Ar—CO); 156.5 (Py); 149.5 (Py); 142.5 (Py); 133.8 (Ar—C—CH$_2$—NH$_2$); 126.0 (Py); 125.9 (Ar); 125.3 (Ar); 123.2 (Py-N—CH—CH); 61.0 (NH$_2$—CH$_2$); 59.0 (Ar—CH$_2$—N); 58.1 (Py-CH$_2$).

ESI mass spectrum, ESI, m/z=791 (M-ClO$_4$)$^+$.

EXAMPLE 3

Preparation of the Ligand Having Formula (III) 6-Amino-N-(3,5-bis((bis(2-pyridylmethyl)amino)methyl)-4-hydroxybenzyl)hexanamide (8) HBPMP-C$_6$NH$_2$

4 +

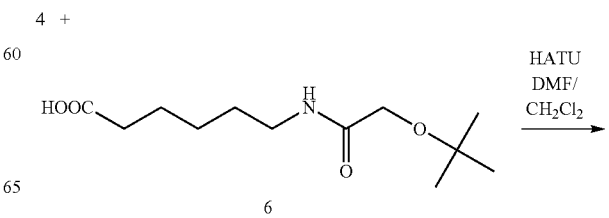

6

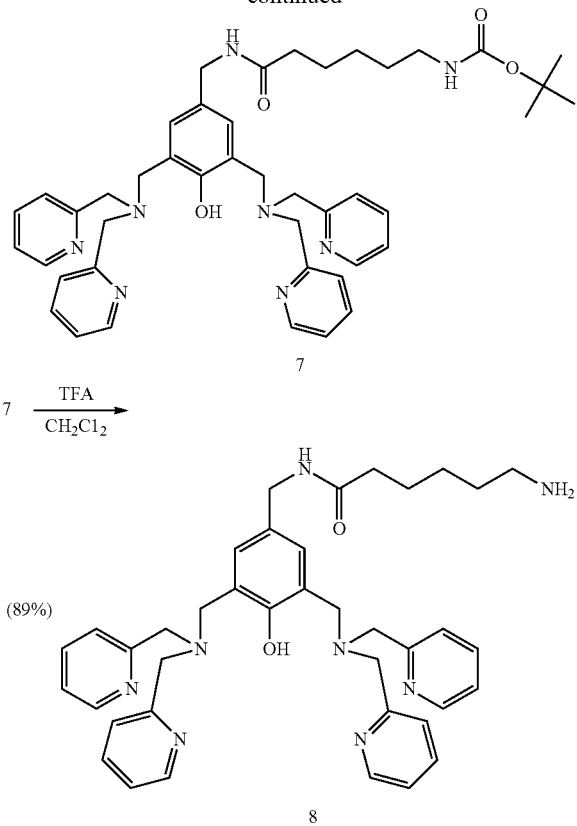

The compound 6 is described in the publication M. B. Doughty et al., 1993, J. Med. Chem., 36, 272-279.

1) 6-tert-butyl-N-(3,5-bis((bis(2-pyridylmethyl)amino)methyl)-4-hydroxybenzylamino)-6-oxohexyl-carbamate (7)

In a three neck 250 ml flask dried in the oven, fitted with an addition funnel and an argon balloon and placed in an ice bath, 835 mg (1.2 equiv.) of 6-tert-butoxycarbonyl-hexanoic acid and 40 mL of dry dichloromethane are introduced. (1.37 g. 1.2 equiv) of HATU (2-(7-Aza-1H-benzotriazole-1-yl)-1,1,3,3-tetramethyluronium hexafluorophosphate) is added to 6 ml of DMF (dimethylformamide) and 1.5 mL (3 equiv.) of triethylamine (NEt₃) before leaving it to be stirred for 30 minutes (still in the ice bath). The ligand 4 (1.52 g, 1 equiv.) dissolved in 40 mL of dry dichloromethane is added therein drop by drop. It is left to be stirred at 0° C. for one hour and then at ambient temperature for one night and one day.

After evaporation of dichloromethane and DMF under vacuum, 4.6 g of a thick oil is obtained which is purified by chromatography on a column of neutral alumina (height: 5.5 cm, diameter 4.5 cm). The column is deactivated by a solution of 2 drops of distilled water with 10 mL of MeOH, 300 mL of EtOAc and 150 mL of cyclohexane. The elution solvents are: EtOAc+cyclohexane, EtOAc, EtOAc+1% to 5% of MeOH.

After evaporation, 1.9 g of a white sticky product is recovered. It is taken up in water, scraped, decanted and extracted with dichloromethane. After drying over $Na_2SO_4$, filtration and evaporation 1.7 g (80%) of the compound 7 is recovered in the form of a beige solid.

$^1$H NMR (300 MHz, $CDCl_3$, TMS, δ ppm): 11.12 (s, 1H, OH); 8.53 (m, 4H, Py); 7.60 (m, 7H, Py); 7.48 (m, 5H, Py); 7.27 (m, 2H Ar); 5.79 (s, 1H, NH); 4.32 (d, 2H, Ar—$CH_2$—NH); 4.13 (d, 4H, Ar—$CH_2$—N); 3.86 (s, 10H, Py-$CH_2$); 2.16 (t, 2H, $CH_2$); 1.86 (d, 5H, $CH_2$); 1.64 (t, 3H, $CH_2$); 1.42 (s, 9H, tBu).

$^{13}$C NMR (75 MHz, $CDCl_3$, TMS, δ ppm): 172.8 ($CH_2$—C=O—NH); 159.4 (O—C=O); 155.8 (Ar—C—OH); 149.2 (Py-N—CH); 136.9 (Py); 129.3 (Ar-CH); 128.3 (O—C—($CH_3$)₃); 124.6 (Ar—C—$CH_2$—NH); 123.3 (Py-C—CH); 122.3 (Py-N—CH—CH); 60.1 (Py-$CH_2$); 55.0 (Ar—$CH_2$); 43.7 (O—CO—NH—$CH_2$); 36.9 (NH—CO—$CH_2$—$CH_2$); 30.1 ($CH_2$); 28.8 ($CH_3$); 26.7 ($CH_2$); 25.6 ($CH_2$).

ESI mass spectrum, m/z=781 (M+Na)⁺, 759 (M+H)⁺

2) 6-amino-N-(3,5-bis((bis(2-pyridylmethyl)amino)methyl)-4-hydroxybenzyl)-hexanamide (8)

In a 250 ml flask fitted with a condenser, 1.69 g of the protected product (7) (1 equiv.) and 200 mL of dry dichloromethane are introduced. The mixture is cooled with an ice bath and then 9 mL of trifluoroacetic acid (46 equiv.) in 10 mL of dry dichloromethane is added drop by drop. The reaction medium is left to be stirred overnight at ambient temperature.

The resulting solution obtained is neutralised up to pH 9 with a 2N sodium hydroxide solution and then with a solution of saturated $NaHCO_3$. The mixture is extracted three times with dichloromethane, and then dried over $Na_2SO_4$, filtered and evaporated. A powder which is dissolved in hot acetonitrile is obtained. After hot filtration, the solution is evaporated and 1.2 g (82%) of the compound 8 is obtained in the form of a pale yellow solid.

$^1$H NMR (300 MHz, $CDCl_3$, TMS, δ ppm): 8.51 (d, 4H, Py); 7.56 (t, 4H, Py); 7.37 (d, 4H, Py); 7.13 (t, 4H, Py), 7.04 (s, 2H Ar); 4.24 (d, 2H, Ar—$CH_2$—NH); 3.83 (s, 8H, Py-$CH_2$) 3.70 (s, 4H, Ar—$CH_2$—N); 2.90 (t, 2H, $CH_2$); 2.24 (t, 2H, $CH_2$); 1.75 (t, 2H, $CH_2$); 1.66 (t, 2H, $CH_2$); 1.26 (t, 2H, $CH_2$).

$^{13}$C NMR (75 MHz, $CDCl_3$, TMS, δ ppm): 172.9 (—C=O); 158.6 (Py-N—CH), 155.0 (Ar—C—OH); 148.8 (Py); 136.7 (Py); 129.4 (Ar—CH); 128.8 (Ar-CH); 122.2 (Py); 123.3 (Py); 122.3 (Py); 59.9 (Py-$CH_2$); 54.7 (Ar—$CH_2$); 42.9 (Ar—$CH_2$—NH—); 39.7 (—$CH_2$—$NH_2$); 35.6 ($CH_2$); 27.6 ($CH_2$); 25.3 ($CH_2$); 24.8 ($CH_2$).

ESI mass spectrum, m/z=681 (M+Na)⁺, 659 (M+H)⁺, 330 (M+2H)²⁺.

EXAMPLE 4

Preparation of the complex [μ-[6-amino-N-(3,5-bis((bis(2-pyridylmethyl)amino)methyl)-4-hydroxybenzyl)hexanamide]]-μ-hydroxo, dizinc, diperchlorate.

(9) [($Zn_2$)(BPMP-$C_6H_2$)(μ-OH)].($ClO_4$)₂

8 $\xrightarrow{Zn(ClO_4)_2, 6 H_2O (2 eq)}{NEt_3/CH_3CN}$

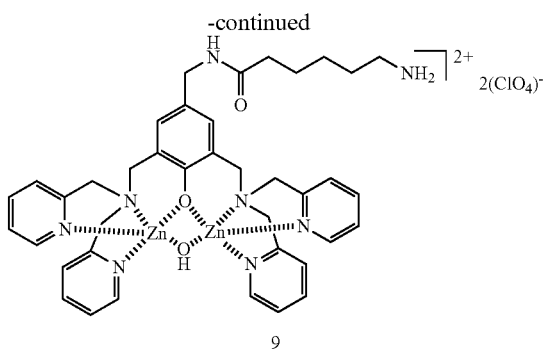

9

In a 100 mL flask the ligand 8 (0.4 g, 1 equiv.) dissolved in 10 mL of acetonitrile (with heating for a little while in order for it to all dissolve) and 0.13 g (2.1 equiv.) of triethylamine are introduced.

0.9 g (2.1 equiv.) of zinc perchlorate hexahydrate dissolved in 4 mL of acetonitrile is added therein drop by drop. Upon completing the addition of perchlorate, the mixture is left to be stirred at ambient temperature for 2 hours. The solution is partially evaporated so as to have a volume of about 5 ml and then ethyl ether is added therein until a certain cloudiness is observed after which it is left at −20° C. overnight.

A precipitate is obtained which is filtered, rinsed with ethyl ether and dried. The filtrate is subjected again to the same treatment, which eventually allows for the recovery of 270 mg (43%) of compound 9 in the form of a pale yellow powder.

$^1$H NMR (300 MHz, DMSO, δ ppm): 8.96 (d, 4H, Py-H); 8.80 (s, 1H, OH), Py-H); 8.11 (t, 4H, Py-H); 7.68 (t, 4H, Py-H), 7.59 (d, 4H, Py-H); 6.83 (s, 2H, Ar—H); 6.64 (s, 1H, NH—CO); 4.01 (s, 8H, Py-CH$_2$); 3.91 (d, 2H, NH$_2$—CH$_2$); 3.84 (s, 4H, Ar—CH$_2$—N); 4.11 (m, 12H, CH$_2$—N); 2.12 (m, 2H, —CH$_2$), 1.52 (m, 4H, —CH$_2$); 1.29 (m, 4H, —CH$_2$).

$^{13}$C NMR (75 MHz, DMSO, δ ppm): 171.4 (—C=O); 155.0 (Py-N—C); 154.9 (Ar—C—OH), 147.5 (Py-CH); 140.8 (Py); 140.2 (Ar—C—CH$_2$—NH$_2$); 130.8 (Ar—CH); 129.8 (Ar—CH); 126.0 (Ar—C); 126.3 (Ar—C); 124.6 (Py-CH); 123.7 (CH); 122.9 (C); 121.1 (CH); 58.8 (Ar—CH$_2$—NH—CO); 57.7 (Ar—CH$_2$—N); 56.7 (Py-CH$_2$), 41.1 (CH$_2$); 35.4 (CH$_2$); 29.7 (CH$_2$); 26.0 (CH$_2$); 25.4 (CH$_2$); 24.6 (CH$_2$).

ESI mass spectrum, m/z=905 (M−ClO$_4$)$^+$, 403 (M−2ClO$_4$)$^{2+}$.

EXAMPLE 5

Colorimetric Assay of Cellular Microparticles by Immobilisation of the Complex from Example 4 on a Microtiter Plate (Sensitivity Study)

a) Reagents:
Glutaraldehyde 25%
Ethanolamine 16.5 M
Bicarbonate buffer (Na Bic), at pH 9.5, 1 M, to be made only by titration of a solution of NaH$_2$CO$_3$ (pH 8.3) with a solution of Na$_2$CO$_3$ at pH 11, 6.
HEPES buffer, 10 mM pH 7.4; 0.15 M NaCl
(hBPMP/Zinc)-C$_6$H$_2$, 150 µM
b) Protocols:
Polymerisation of glutaraldehyde:
50 ml of a solution of 2.5% glutaraldehyde is prepared in 0.1 M Na Bic, then the mixture is placed in a sealed vial at 37° C. for 2 hours.

Adsorption of polyglutaraldehyde on the surface of polyvinyl chloride:
A microtiter plate with 96 wells is used.
100 µL of 2.5% glutaraldehyde is deposited in each well and left for 2 hours at 22° C. The polyglutaraldehyde is removed and the surface is rinsed 3 times with water.
Immobilisation of the complex [(Zn$_2$)(BPMP-C$_6$H$_2$)(µ-OH)].(ClO$_4$)$_2$
The complex in 0.1 M HEPES, pH 8.2 is immobilised on the surface of the polyvinyl chloride plate for 24 hours at +22° C.:
The free aldehyde groups are saturated with 0.3 M ethanolamine by incubating the surface with this solution for 2 hours at 22° C., then the ethanolamine is eliminated by washing with water and then washing 3 times in 10 mM HEPES at pH 7.4, 0.15 M NaCl. The plates are stored at 4° C.
A buffer solution (10 mM HEPES, 0.9% NaCl) containing the microparticles is incubated for 12 hours, and the plates are then rinsed with the buffer solution. The microparticles are derived from the activation of the cell culture of HMEC1 human microvascular endothelial cells by TNF-α, as described in R. Lacroix et al., Blood, 2007, 110, 2432-2439.

c) Detection
The detection is carried out by means of photometric analysis. Incubation is performed for 3 hours with an anti-CD105 antibody that is specific to the microparticles being studied, and thereafter rinsing with 10 mM HEPES+40 mg/ml BSA is carried out.
Subsequently incubation is performed with the secondary antibody coupled to peroxidase, after which rinsing with 10 mM HEPES+40 mg/ml BSA is carried out.
The detection is carried out with ABTS (2,2'-azino-bis(3-ethylbenzothiazoline-6-sulfonic acid) 1 mg/ml if a secondary antibody coupled to peroxidase is used.
The reading is performed by means of a spectrophotometer.
The results are reported in FIG. 1 which represents the detection by photometric analysis of a dilution of microparticles that is based on the amount of proteins.
The resulting signal is expressed in mOD/min corresponding to the initial velocity (Vi) of the reaction of degradation of the substrate by peroxidase.
The signal obtained based on the quantity of microparticles shows a specific dose-response.

EXAMPLE 6

Study of the Specificity of the Zn Complexes from Examples 2 And 4 by Immunochemical Method on a Microtiter Plate A solution of 2.5% glutaraldehyde diluted in Na Bic (0.1 M, pH 9.5) was placed in each well of the microtiter plate and left for 4 hours at 22° C. After the elimination of glutaraldehyde and several rinses with water, the complex to be tested, namely [(Zn$_2$)(BPMP-NH$_2$)(µ-OH)].(ClO$_4$)$_2$ (Example 2) or [(Zn$_2$)(BPMP-C$_6$H$_2$)(µ-OH)].(ClO$_4$)$_2$ (Example 4), was incubated at a concentration of 500 nm (concentration determined by titration). Then, the complex was eliminated by rinsing with a 10 mM HEPES solution. Finally, the free aldehyde groups were saturated with a solution of 0.3 M ethanolamine followed by several rinses with the 10 mM HEPES buffer.
A buffer solution (10 mM HEPES, 0.9% NaCl) containing microparticles (resulting from the activation of the cell culture of HMEC1 cells) was subsequently incubated for 1 hour and then eliminated by rinsing with the buffer solution.

An indirect immunochemical method (primary anti-CD105 antibody at 1 µg/ml; secondary antibody coupled to peroxidase at 160 ng/ml and 1 mg/ml ABTS) was used to analyse the presence of the endothelial antigen CD105 on the microparticles.

The reading is performed by means of a spectrophotometer at 405 nm.

Figure 2:
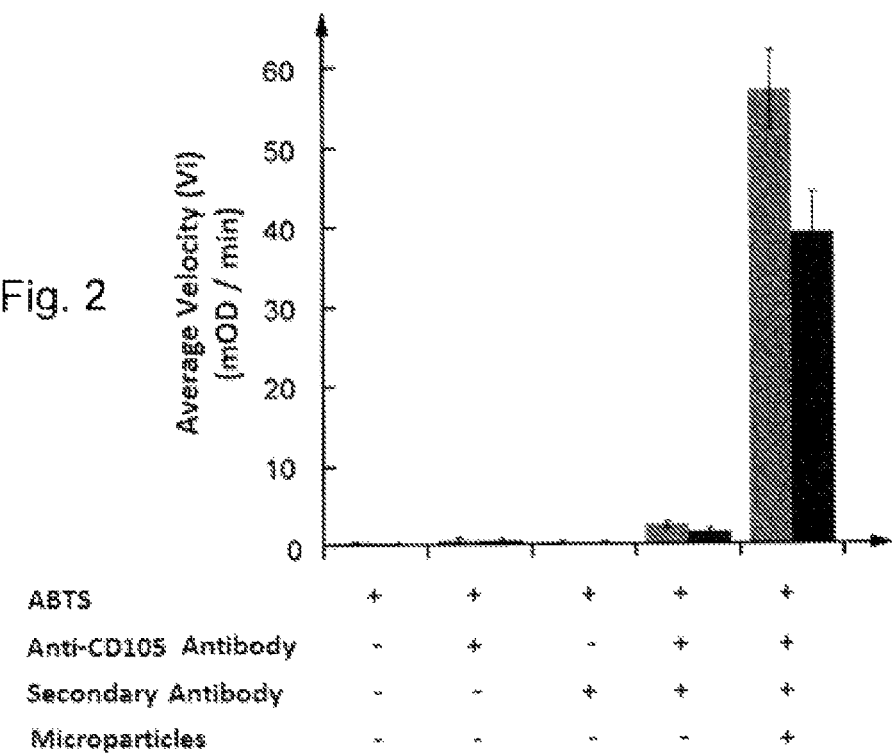
FIG. 2 shows the detection of a dilution of microparticles that is based on the amount of proteins, by photometric analysis, in order to study the specificity of the Zn complexes of the invention (immunochemical method on a microtiter plate).

The results are reported in FIG. 2, which represents the detection by photometric analysis of a dilution of microparticles that is based on the amount of proteins.

The resulting signal is expressed in mOD/min corresponding to the initial velocity (Vi) of the reaction of degradation of the substrate by peroxidase and is shown in dark gray for the complex from Example 2, and in light gray for the complex from Example 4.

The presence (+ sign) or absence (− sign) of the reagents in the measurement medium is indicated below the abscissa axis.

The signal obtained shows that the complex according to the invention specifically recognises the microparticles in an immunochemical revelation process;

In addition, the methodology seems to generate only a very low background noise, as shown by the very low signal measured in the absence of microparticles.

EXAMPLE 7

Preparation of the complexe [µ-[4-(aminomethyl)-2,6-bis[[bis(2-pyridylmethyl)amino]methyl]-phenolato]]-µ-hydroxo, dicopper, diperchlorate. (10) [(Cu$_2$)(BPMP-NH$_2$)(µ-OH)].(ClO$_4$)$_2$

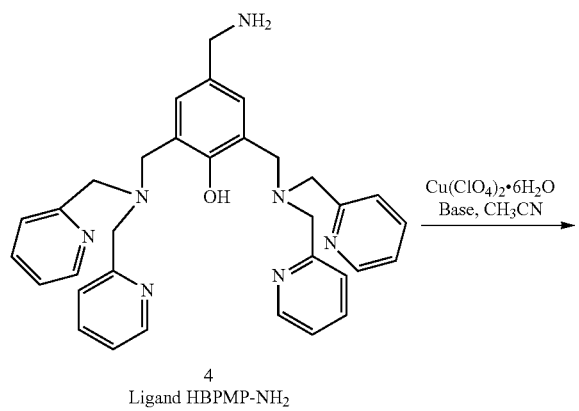

4
Ligand HBPMP-NH$_2$

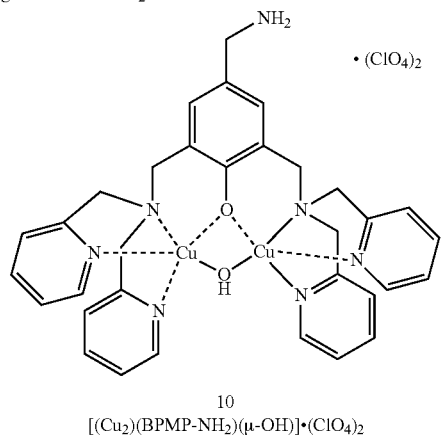

10
[(Cu$_2$)(BPMP-NH$_2$)(µ-OH)]•(ClO$_4$)$_2$

In a 25 mL flask the ligand 4 (0.146 g, 1 equiv.) dissolved in 10 mL of acetonitrile and 77 µl (2 equiv.) of triethylamine is introduced.

0.21 g (2 equiv.) of cupric perchlorate hexahydrate dissolved in 3 mL of acetonitrile is added therein drop by drop. Upon completing the addition of the copper salt, the mixture is left to be stirred at ambient temperature for 30 minutes. The solution is partially evaporated so as to have a volume of about 5 mL and then tetrahydrofuran is added therein until a certain cloudiness is observed after which it is left at −20° C. for three days.

A precipitate is obtained which is filtered and then rinsed with ethyl ether. The solid recovered is redissolved in acetonitrile and reprecipitated as before with tetrahydrofuran at −20° C. After filtration, rinsing and drying, 118 mg (36%) of the compound 10 is recovered in form of a green powder.

ESI mass spectrum, m/z=806 (z=1) [M−ClO$_4^-$+H$_2$O]; 353.5 (z=2) [M−2ClO$_4^-$+2H$_2$O]; UV/vis (DMSO/water, pH=7; 30/70): $\lambda_{max}$ ($\epsilon$)≈340 (sh), 425 (sh), 700 (191 M$^{-1}$cm$^{-1}$).

EXAMPLE 8

Preparation of the complex [µ-[6-amino-N-(3,5-bis((bis(2-pyridylmethyl)amino)methyl)-4-hydroxybenzyl)hexanamide]]-µ-hydroxo, dicopper, diperchlorate. (11) [(Cu$_2$)(BPMP-C$_6$H$_2$)(µ-OH)].(ClO$_4$)$_2$

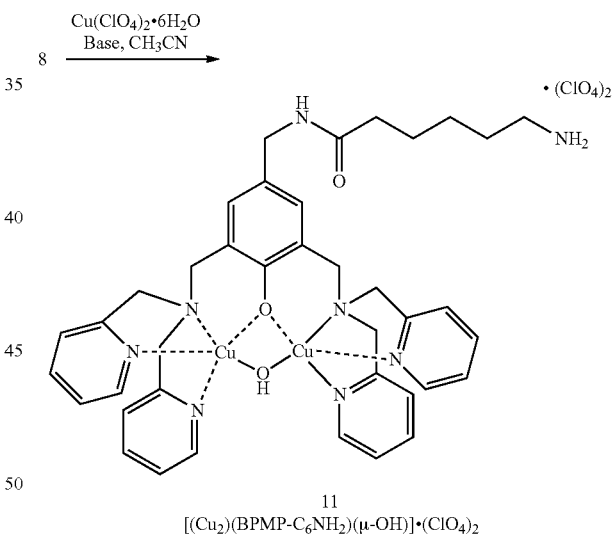

11
[(Cu$_2$)(BPMP-C$_6$NH$_2$)(µ-OH)]•(ClO$_4$)$_2$

In a 25 mL flask the ligand 8 (0.350 g, 1 equiv.) dissolved in 12 mL of acetonitrile and 0.118 g (2.2 equiv.) of triethylamine are introduced.

0.43 g (2.1 equiv.) of cupric perchlorate hexahydrate dissolved in 8 mL of acetonitrile is added therein drop by drop. Upon completing the addition of the copper salt, the mixture is left to be stirred at ambient temperature for 1 hour. The solution is partially evaporated so as to have a volume of about 5 ml and then tetrahydrofuran is added therein until a certain cloudiness is observed after which it is left at −20° C.

A thick oil gets deposited. The supernatant is removed and 5 ml of ethyl ether is added and the oil is scraped with a glass rod. A green powder precipitates: it is filtered, rinsed with ethyl ether and dried. The filtrate is returned to −20° C. and a second fraction of oil is deposited. It is treated as previously described. This eventually allows for the recovery of 246 mg (46%) of the compound 11 in the form of a green powder.

ESI mass spectrum, m/z=400 (z=2) [M−2ClO$_4$]; UV/vis (DMSO/water, pH=7; 30/70): $\lambda_{max}$ ($\epsilon$)≈350 (sh), 450 (316), 700 (202 M$^{-1}$cm$^{-1}$).

EXAMPLE 9

Preparation of the Ligand Having Formula (III)

6-amino-N-(3,5-bis((bis(2-pyridylethyl)amino)methyl)-4-hydroxybenzyl)-hexanamide (12) HBPEP-C$_6$H$_2$ The ligand 12 is prepared in a manner similar to that for the ligand 8 in four steps from compound 1 on which the bis(2-pyridylethyl) amine is condensed and whose preparation is described in the publication of M A Halcrow et al, 2003, Dalton Trans, 4224-4225.

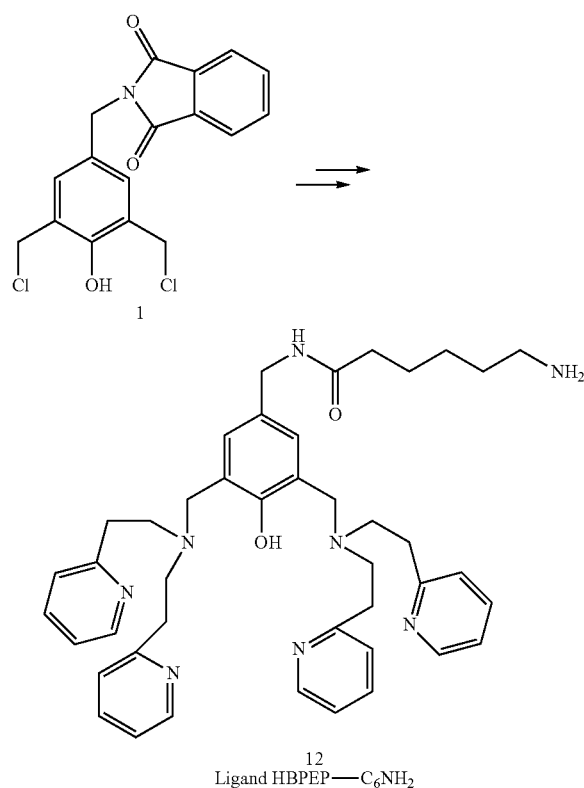

12
Ligand HBPEP—C$_6$NH$_2$ $^1$H NMR (300, CDCl$_3$, δ ppm): 8.42 (d, 4H, Py-H); 7.52 (td, 4H, Py-H); 7.07 (m, 8H, Py-H); 6.93 (s, 2H, Ar—H); 6.85 (t, 1H, NH—CO); 4.22 (d, 2H, Ar—CH$_2$—NH—); 3.80 (s, 4H, Ar—CH$_2$—N); 2.99 (m, 16H, Py-CH$_2$—CH$_2$—N); 2.79 (m, 2H, NH$_2$—CH$_2$); 2.16 (t, 2H, CO—CH$_2$), 1.58 (m, 4H, —CH$_2$); 1.32 (m, 2H, —CH$_2$).

$^{13}$C NMR (75 MHz, CDCl$_3$, δ ppm): 172.9 (—C=O); 159.6 (Py-N—C); 155.3 (Ar—C—OH), 149.0 (Py-N—CH); 136.4 (Py-C); 128.6 (Ar—C—CH$_2$—NH); 128.4 Ar—CH; 123.4 (Py-N—CH—CH); 122.8 (Ar—C—CH$_2$—N); 121.3 (Py-CH$_2$—CH$_2$); 54.7 (Ar—CH$_2$—NH); 53.3 (Py-CH$_2$—CH$_2$); 42.9 (Ar—CH$_2$—NH); 40.0 (NH$_2$—CH$_2$); 35.7 (CO—CH$_2$); 34.8 (Py-CH$_2$—CH$_2$); 28.3 (NH$_2$—CH$_2$—CH$_2$); 25.5 (CH$_2$); 24.8 (CH$_2$).

ESI mass spectrum, m/z=715 [M+H$^+$]

EXAMPLE 10

Preparation of the complexe [μ-[6-amino-N-(3,5-bis((bis(2-pyridylethyl)amino)methyl)-4-hydroxybenzyl)hexanamide]]-μ-hydroxo, dizinc, diperchlorate.
(13) [(Zn$_2$)(BPEP-C$_6$H$_2$)(μ-OH)]·(ClO$_4$)$_2$.

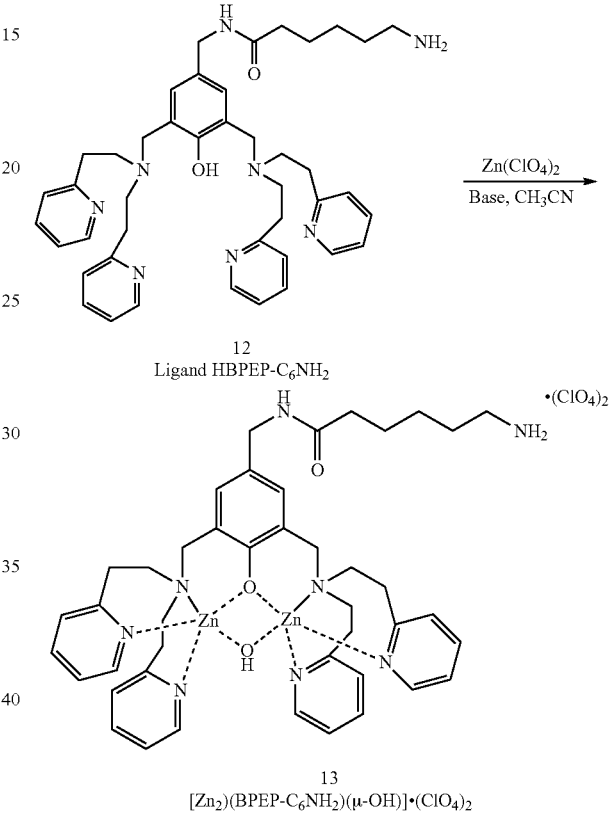

13
[Zn$_2$)(BPEP-C$_6$NH$_2$)(μ-OH)]·(ClO$_4$)$_2$

In a 50 mL flask the ligand 12 (551 mg, 0.77 mmol, 1 equiv.) dissolved in 15 mL of acetonitrile and 280 μL (2.5 equiv.) of triethylamine is introduced. 724 mg zinc perchlorate hexahydrate (2.5 equiv.) dissolved in 8 mL of acetonitrile is added therein drop by drop. Upon completing the addition of the zinc salt, the mixture is left to be stirred at ambient temperature for 5 hours. The solution is partially evaporated so as to have a volume of about 5 mL and then tetrahydrofuran is added therein until a certain cloudiness is observed after which it is left at −20° C. overnight.

A pasty precipitate is obtained which is filtered, rinsed with ethyl ether and dried. A solid is recovered which is scraped with a glass rod in the presence of ethyl ether and then the solution is removed and the operation is repeated three more times. After drying, this eventually allows for the recovery of 218 mg (27%) of the compound 13 in the form of a pale yellow solid.

$^1$H NMR (400 MHz, CD$_3$CN+DMSO, δ ppm): 8.48 (d, 4H, Py-H); 7.99 (m, 4H, Py-H); 7.45 (m, 8H, Py-H); 7.40 (s, 1H, NH—CO); 6.86 (s, 2H, Ar—H); 4.05 (s, 2H, Ar—CH$_2$—NH—); 3.62 (t, 4H, Ar—CH$_2$—N); 3.05 (m, 8H, Py-CH$_2$—CH$_2$—N); 2.79 (m, 10H, NH$_2$—CH$_2$, Py-CH$_2$); 2.09 (t, 2H, CO—CH$_2$), 1.56 (m, 4H, —CH$_2$); 1.30 (m, 2H, —CH$_2$).

$^{13}$C NMR (100 MHz, CD$_3$CN+DMSO, δ ppm): 173.1 (—C═O); 161.6 (Py-N—C); 158.3 (Ar—C—OH), 149.7 (Py-N—CH); 141.8 (Py-C); 132.0 (Ar—C—CH$_2$—NH$_2$); 132.0 Ar—CH); 126.3 (Py-N—CH—CH); 124.7 (Py-N—C—CH); 123.1 (Ar—C—CH$_2$—N); 47.3 (Py-CH$_2$—CH$_2$); 36.2 (Py-CH$_2$); 32.7 (CO—CH$_2$); 27.5 (NH$_2$—CH$_2$); 26.5 (CO—CH$_2$—CH$_2$); 25.6 (CH$_2$).

ESI mass spectrum, m/z; 961 (z=1) [M–ClO$_4$]; 431 (z=2) [M–2ClO$_4$]

EXAMPLE 11

Study of the Sensitivity of the System of Microparticle Detection—Revelation by the Zn Complex from Examples 4 and 10 and the Cu Complex of from Example 8 by Measuring the Generation of Plasmin The principle of the measurement is based on measuring the fibrinolytic activity resulting from the generation of plasmin by the microparticles derived from the activation of the HMEC1 cell culture. These microparticles carry urokinase (or plasminogen activator enzyme—uPA) on their surface, which enables the conversion of plasminogen to plasmin, which lyses the fibrin.

The generation of plasmin is detected by the cleavage of a chromogenic substrate, namely methylmalonyl-hydroxypropyl-arginyl-paranitroanilide (CBS) by plasmin (spectrophotometric measurement).

a) Protocols
Preparation of the microtiter plate
A 96 well PVC U bottom plate is used.
An assay buffer of the following composition is prepared:

| | Stock Solution | Volume of stock for 1 litre buffer | Final Solution |
|---|---|---|---|
| Phosphate pH = 7.4 | 0.5M | 100 ml | 50 mM |
| NaCl | 5M | 16 ml | 80 mM |
| BSA | 40 g/l | 2 g or 50 ml at 40% | 2 g/l |
| Tween 20 | 10% | 1 ml | 0.01% |
| NaN$_3$ or thimerosal | 10% | 1 ml | 0.01% |
| H$_2$O qs (quantity sufficient for) | | H$_2$O qs 832 ml | |

Incubation is carried out using 150 μL of assay buffer per well for 30 min at ambient temperature.

Preparation of 4 μM plasminogen for an entire plate
48.3 μl of a stock solution of 103.5 μM plasminogen is used and 1201.7 μl of assay buffer is added therein.

Preparation of 3 mM CBS0065 for an entire plate
A stock solution of 7.5 mM CBS0065 is used and 750 μl of assay buffer is added therein.

b) Detection
The plate containing the assay buffer is reversed so as to empty the wells, and then dried with paper towels.

The 4 μM plasminogen solution is mixed with the 3 mM CBS0065 solution, followed by incubation of 25 μl of a buffer solution (10 mM HEPES, 0.9% NaCl) containing the microparticles (derived from the activation of the HMEC1 cell culture) for 1 hour at 37° C. Thereafter 12.5 μl of CBS0065 and 12.5 μl of plasminogen (respectively 2 μM and 1.5 mM final concentration) are added, and the plate is sealed.

The reading is performed by means of a spectrophotometer at 405 nm and 490 nm at 37° C. for 18 hours.

Figure 3:
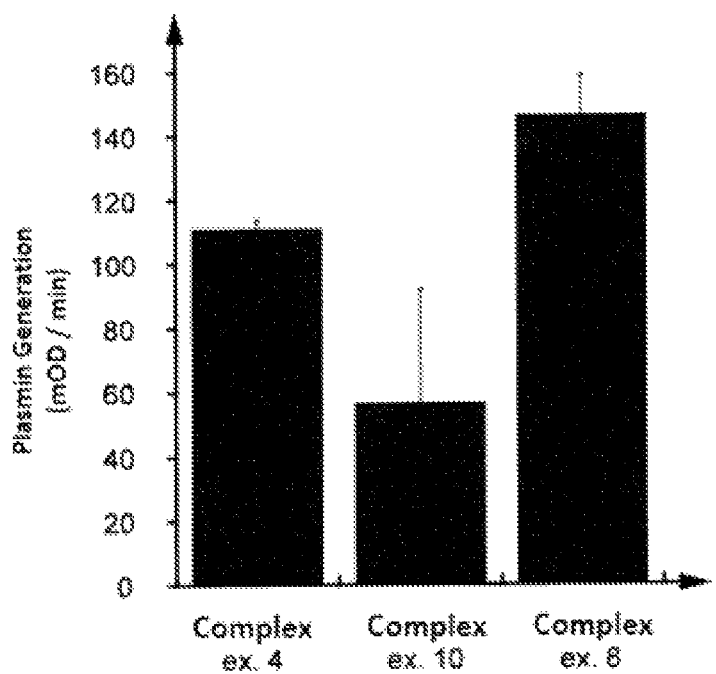
FIG. 3 shows the detection of plasmin generation by assaying the fibrinolytic activity resulting from the generation of plasmin by the microparticles derived from the activation of the HMEC1 cell culture. This assay studies the sensitivity of the system of microparticle detection—revelation by Zn and Cu complexes of the invention

The results are reported in FIG. 3, which represents the detection of plasmin generation by assaying the fibrinolytic activity.

The signal obtained is expressed in mOD/min.

The results show that the immobilisation of microparticles by the metal complexes according to the invention enables their functional assay. A variation in the results may also be observed depending on the length of the "arm" bound to the pyridine group and the type of metal ion.

The invention claimed is:

1. A compound having formula (I) or formula (II):

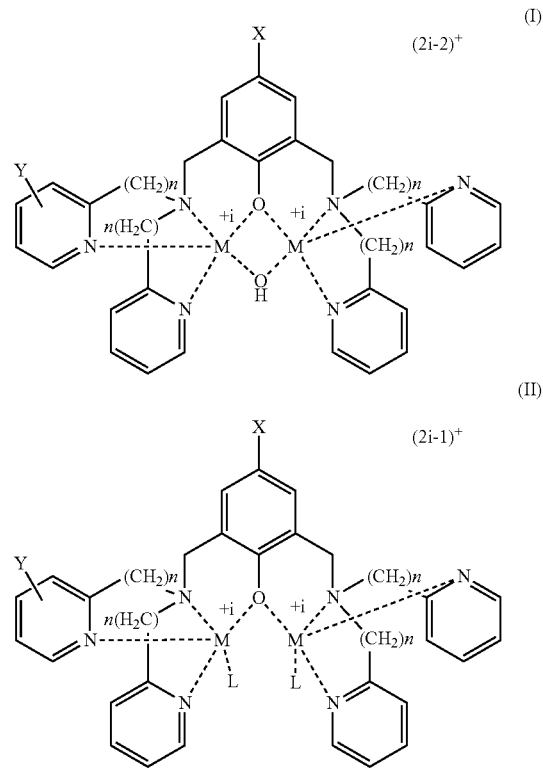

wherein
M$^{+i}$ is a metal ion, and i is 1, 2 or 3;
L is an exchangeable ligand;
X is a —(CH$_2$)$_m$—NH-A group, or a —CH$_2$—NHC(O)—R—NH-A group wherein R is a C$_2$-C$_{10}$ alkyl group, preferably a C$_6$-C$_{10}$ alkyl group, either substituted or unsubstituted, linear or branched, and A is H or a fluorophore group;
m=1 to 12;
n=1, 2 or 3; and
Y is —(CH$_2$)$_p$—NH$_2$ wherein p=0 to 12.

2. A compound having formula (I) or formula (II) according to claim 1, characterised in that M is selected from Zn, Cu, Mn, Co, Ni and Fe.

3. A compound according to claim 1 having formula (I) or (II) wherein:
M is Zn or Cu;
X is —(CH$_2$)$_m$—NH-A, where m=1, A is H, n=1 and p=0; or
X is —(CH$_2$)$_m$—NH-A, where m=1, A is H, n=2 and p=0; or
X is —CH$_2$—NHC(O)—R—NH-A, A is H, n=1 and p=0.

4. A compound having formula (I) or formula (II) according to claim 1, wherein X is —(CH$_2$)$_m$—NH-A, —CH$_2$—NHC(O)—R—NH-A wherein R is a C$_2$-C$_{10}$ alkyl group, preferably a C$_6$-C$_{10}$ alkyl group, either substituted or unsubstituted, linear or branched, and A is a fluorophore group.

5. A compound having formula (III)

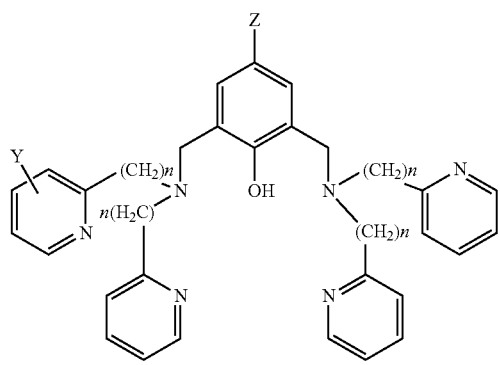

(III)

wherein
Z is NH$_2$ or a —(CH$_2$)$_m$—NH-A group, or a —CH$_2$—NHC(O)—R—NH-A group wherein R is a C$_2$-C$_{10}$ alkyl group, preferably a C$_6$-C$_{10}$ alkyl group, either substituted or unsubstituted, linear or branched, and A is H or a fluorophore group, provided that when m=2, A is not H;
m=1 to 12;
n=1, 2 or 3; and
Y is (CH$_2$)$_p$—NH$_2$ wherein p=0 to 12.

6. A compound having formula (III) according to claim 5, wherein
z is —(CH$_2$)$_m$—NH-A, where m=1, A is H, n=1 and p=0; or
z is —(CH$_2$)$_m$—NH-A, where m=1, A is H, n=2 and p=0; or
z is —CH$_2$—NHC(O)—R—NH-A, A is H, n=1 and p=0.

* * * * *